United States Patent
Gray, Jr.

[11] Patent Number: 6,126,694
[45] Date of Patent: Oct. 3, 2000

[54] UNIVERSAL DISTAL BROACH AND STEM TRIAL

[75] Inventor: Wayne P. Gray, Jr., Pflugerville, Tex.

[73] Assignee: Sulzer Orthopedics Inc., Austin, Tex.

[21] Appl. No.: 09/263,707

[22] Filed: Mar. 5, 1999

[51] Int. Cl.[7] .................................................. A61F 2/32
[52] U.S. Cl. ........................ 623/22.11; 623/23.22
[58] Field of Search ........................ 623/16, 18, 20; 606/85, 86, 102

[56] References Cited

U.S. PATENT DOCUMENTS

| | | | |
|---|---|---|---|
| 2,947,308 | 8/1960 | Gorman | 623/22 |
| 4,601,289 | 7/1986 | Chiarizzio et al. | 606/85 |
| 4,765,328 | 8/1988 | Keller et al. | 606/85 |
| 4,944,763 | 7/1990 | Willert et al. | 623/23 |
| 4,990,149 | 2/1991 | Fallin | 606/85 |
| 5,002,581 | 3/1991 | Paxson et al. | 623/23 |
| 5,089,004 | 2/1992 | Averill et al. | 606/85 |
| 5,135,529 | 8/1992 | Paxson et al. | 606/85 |
| 5,376,123 | 12/1994 | Klaue et al. | 623/23 |
| 5,389,107 | 2/1995 | Nassar et al. | 623/23 |
| 5,441,501 | 8/1995 | Kenyon | 606/85 |
| 5,496,323 | 3/1996 | Dye | 606/79 |
| 5,607,431 | 3/1997 | Dudasik | 606/80 |
| 5,702,456 | 12/1997 | Pienkowski | 623/18 |
| 5,766,261 | 6/1998 | Neal et al. | 623/16 |
| 5,814,049 | 9/1998 | Pratt et al. | 606/80 |
| 5,888,211 | 3/1999 | Sanders | 623/23 |
| 5,906,644 | 5/1999 | Powell | 623/23 |
| 5,993,455 | 11/1999 | Noble | 606/85 |

*Primary Examiner*—Paul J. Hirsch
*Assistant Examiner*—Michael B. Priddy
*Attorney, Agent, or Firm*—Philip S. Lyren; Kenneth S. Barrow

[57] ABSTRACT

A combination stem trial and broach includes a broach having a first attachment device at one end thereof. The first attachment device includes a first threaded member and a first orientation member. An elongated stem trial has a second attachment device at a first end thereof for engagement with the first attachment device. The second attachment device includes a second threaded member for connection with the first threaded member and a second orientation member for connection with the first orientation member.

23 Claims, 4 Drawing Sheets

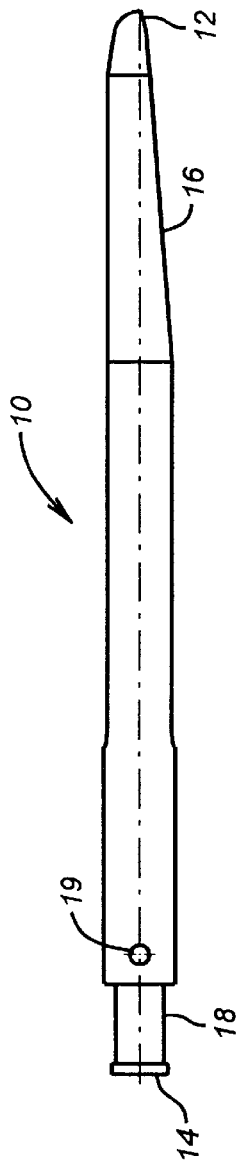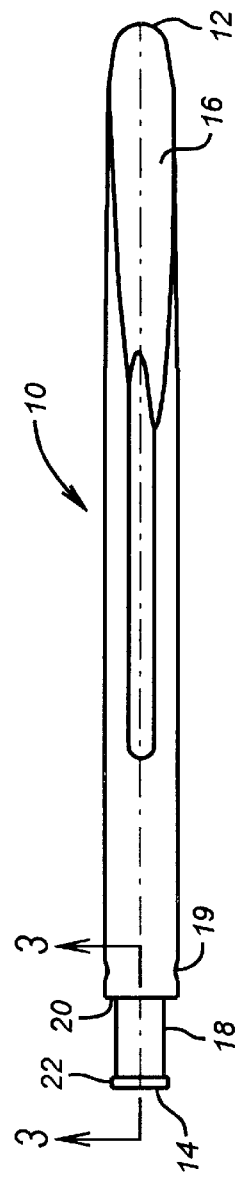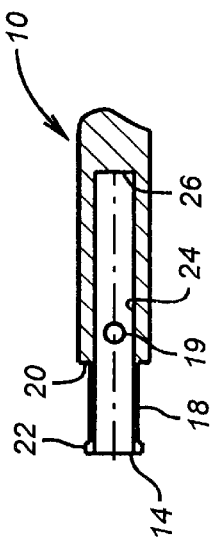

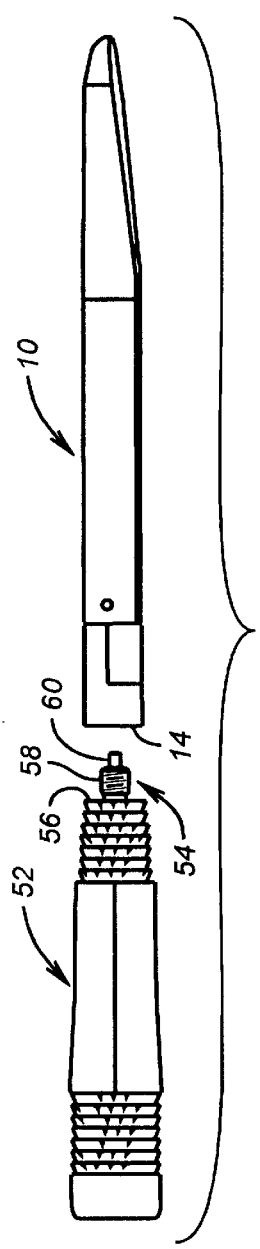
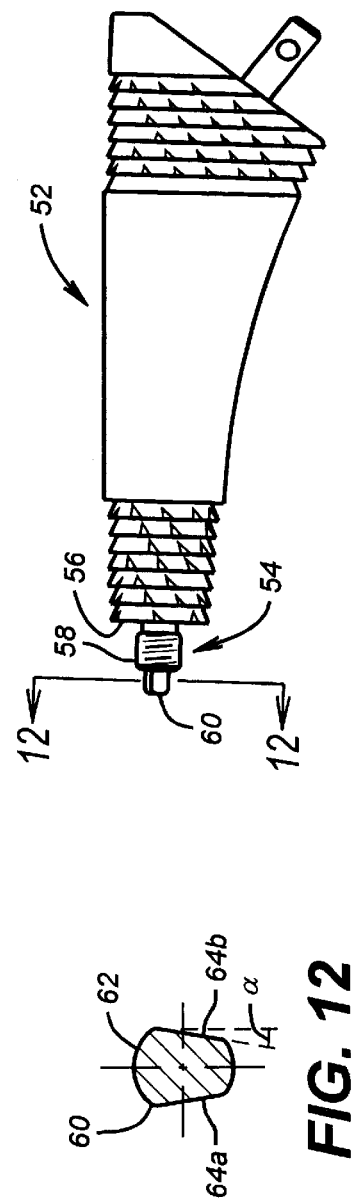
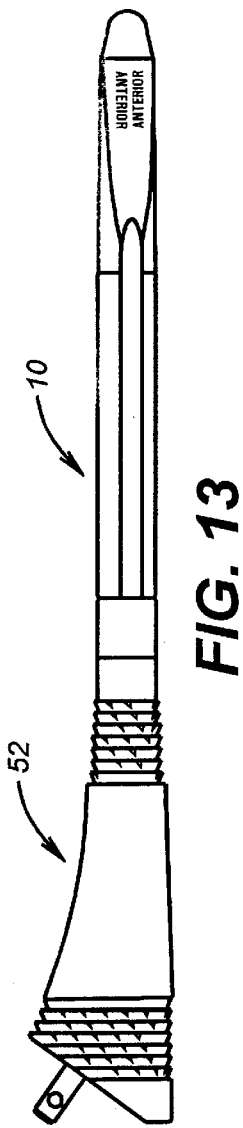
FIG. 10
FIG. 11
FIG. 12
FIG. 13

UNIVERSAL DISTAL BROACH AND STEM TRIAL

BACKGROUND

The disclosures herein relate generally to implantable prostheses for replacing human skeletal joints, and more particularly to a universal distal broach and implant stem trial for sizing left and right femurs.

Implantable orthopedic prostheses, in one form, comprise manufactured replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the hip joint is one of the joints most often treated with such prostheses. The hip joint is a major weight bearing joint and degenerates relatively quickly in case of abnormality. Also, the hip joint plays a critical role in ambulation and quality of life, resulting in great demand for surgical correction of abnormalities.

The human hip joint involves two bones: the femur and the pelvis, each having a smooth articulation surface arranged for articulation against an adjacent articulation surface of the other bone. The femur includes at its proximal extremity a head having a convex, generally spherically contoured articulation surface. The pelvis, in pertinent part, includes an acetabulum having a concave, generally spherically contoured articulation surface. The mutually engaging articulation surfaces of the femur and the pelvis together form, functionally, a ball-and-socket joint.

As used herein, the words proximal and distal are terms of reference that indicate a particular portion of a prosthesis component according to the relative disposition of the portion when the component is implanted. "Proximal" indicates that portion of a component nearest the torso, whereas, "distal" indicates that portion of the component farthest from the torso. Directional terms of reference used herein include superior, inferior, anterior, posterior, medial and lateral, which are used according to their commonly understood anatomical meanings. More particularly, with regard to a person in a standing position, superior means upward, inferior means downward, anterior means forward, posterior means rearward, medial means inwardly from the side toward the center of the body, and lateral means outwardly from the center of the body toward the side.

One or both of the articulation surfaces of the hip joint may fail to act properly, requiring the defective natural articulation surface to be replaced with a prosthetic articulation surface provided by an implantable prosthesis. To fit defects of varying scope, while allowing healthy portions of the hip joint to be conserved, a range of types of orthopedic implants is available. The range extends from total hip prosthesis systems for replacing the articulation surfaces of both the femur and the pelvis, to less comprehensive systems for replacing only the femoral articulation surface. Commonly employed orthopedic hip prostheses include components that fall within one of three principle categories: femoral stems, femoral heads and acetabular cups. A so-called "total" hip prosthesis includes components from each of these categories. The femoral stem replaces the proximal end of the femur and includes a distal stem received within the medullary canal at the proximal end of the femur. The femoral head replaces the natural head and articulating surface of the femur. The acetabular cup replaces the natural socket and articulating surface of the acetabulum of the pelvis. In some designs, the stem and head are an integral, unitary component, but more often the stem and head are separate modular components designed to be assembled to suit the anatomical needs of the patient. A so-called "bipolar" hip prosthesis includes only femoral stem and head components. The femoral part of the hip joint is replaced with a femoral stem supporting an artificial femoral head. The latter includes an inner head, fixed to the femoral stem, that articulates within an outer head. The outer head articulates directly against the natural acetabulum. Similarly, a so-called "unipolar" hip prosthesis also includes only femoral stem and head components. The femoral part of the hip joint is replaced with a femoral stem supporting an artificial femoral head. The femoral head articulates directly against the natural acetabulum while remaining fixed relative to the femoral stem.

The acetabular cup component of a total hip prosthesis is configured to be received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component. The head articulates in the bearing cavity as a ball-and-socket joint to restore motion to a defective hip joint. One common type of acetabular cup involves an acetabular shell made of a bio-compatible metal such as titanium or a titanium alloy, and a bearing insert made of a bio-compatible polymer such as ultra-high molecular weight polyethylene. The acetabular shell is shaped generally as a hemispherical cup having a dome, or apex, at a proximal end and an annular rim at a distal end. The acetabular shell includes a concave distal surface between the apex and annular rim that defines a shell cavity having an opening at the rim of the cup for receiving the bearing insert. The bearing insert has a generally convex proximal surface for receipt and fixation within the acetabular shell in generally congruent engagement with the concave distal surface of the shell wall. The bearing insert also has a bearing cavity that opens distally for receiving the head of the femoral component. The bearing cavity is defined by a generally spherical concave bearing surface having a radius similar to that of the femoral head component. The concave bearing surface articulates against the surface of the spherical femoral head component. The acetabular shell can be affixed to the acetabular bone by bone screws or bone cement. If bone screws are elected, the screws are driven into the bone through the screw holes before the bearing insert is placed into the shell. The shell also can be affixed by a combination of a bone screws and bone cement.

The femoral stem component typically is constructed as an integral unit having a distal stem, a proximal body and neck. The distal stem is relatively elongated and generally cylindrical or slightly conical and sized to fit within the relatively narrow intra medullary canal near the proximal end of the femur. The proximal body extends superiorly from the proximal end of the distal stem and is sized to fit within and substantially fill the expanded intramedullary canal at the proximal end of the femur. The neck extends superiorly and medially from the proximal body at an angle of about 45°. The orientation of the neck is designed to replicate the natural orientation of the natural neck of the femur. The proximal end of the neck typically is configured as a male conical taper, or Morse taper, for frictionally interlocking with a mating female conical taper formed in the prosthetic femoral head. The femoral stem can be affixed to the femoral bone surrounding the intramedullary canal by bone cement and rely on bone growth adjacent the implant to secure the implant in place.

The femoral head component is configured substantially as a polished sphere having a blind hole therein shaped as a female conical taper, or Morse taper, for frictionally interlocking with the male conical taper of the neck. The femoral head can also include an integral boss surrounding the blind hole and extending from the head, permitting the offset of the head relative to the femoral stem to be increased.

To implant the femoral stem component, a typical surgical procedure involves resecting the natural neck and head of the proximal femur by performing an osteotomy along a plane oriented substantially perpendicular to the axis of the natural neck. The natural head and neck is removed, exposing the proximal medullary canal of the femur. Specially configured instruments are used to remove cancellous bone from the proximal intramedullary canal and shape a cavity within the cancellous bone that is closely complementary to the external shape of the femoral component. If permitted by the patient's anatomy, it is desirable to enlarge the cavity to the inner wall of the cortical bone and use a prosthesis large enough to engage the cortical bone. This provides secure fixation of and support for the femoral stem.

The cavity that is to be formed in the proximal intramedullary canal is generally elongated and cylindrical or slightly conical at the distal end, and generally oval or trapezoidal in cross-section and tapered longitudinally at the proximal end. To form such a cavity, it is common to employ a rotary reamer to ream the distal portion of the cavity. The rotary reamer is then withdrawn and a broach, shaped like the proximal portion of the femoral component, is repeatedly driven into the proximal intramedullary canal. The broach usually has a stem extension that extends into the previously reamed distal portion of the cavity to serve as a pilot to guide the broach, the proximal portion of which is fitted with cutting surfaces. Often, the pilot stem pistoning in the reamed distal portion of the cavity does not provide enough directional stability to assure that the broached proximal portion of the cavity is well aligned with the reamed distal portion of the canal. The result is a cavity that may not conform as closely to the external shape of the femoral implant as desired.

Prior to implanting the femoral stem, it is useful for the surgeon to be able to confirm that the bone cavity has been reamed to the proper depth. The provides assurance that the center of rotation of the femoral head will be properly located to restore the hip joint to an anatomically correct condition. One method of confirmation is to withdraw the broach and insert a trial femoral stem component into the reamed and broached cavity, and to perform a trial reduction of a joint using a trial femoral head on the trial stem. If the trial reduction indicates that further broaching or reaming of the cavity is required, the trial stem must be withdrawn, the broach must be reinserted, and the procedure must be repeated. To reduce the complexity of the procedure, it is also known to use a broach having means to which a trial femoral head can be attached, thereby permitting the trial reduction to be performed while leaving the broach in place to serve as the trial stem.

In U.S. Pat. No. 5,607,431, a surgical instrument system for preparing the medullary canal of the femur for implanting a prosthetic femoral component includes a template to be used in determining osteotomy position from an x-ray. A gauge is provided to locate and mark this position on the anterior femur. A distal reamer having an elongated drive shaft is used to form the canal to receive the distal stem of the femoral component. A metaphyseal template is used to determine the proper anteversion/retroversion and a chisel is used to cut the lateral area of the femur, both of which are guided by the elongated reamer shaft. A proximal broach also guided by the reamer shaft is used to shape the proximal medullary canal.

Therefore, what is needed is a universal distal broach and implant stem trial which can be used in either the left or right femur, and therefore reduce the instrumentation inventory.

SUMMARY

One embodiment, accordingly, provides for using a proximal broach for attachment to a distal stem in alignment for either a right or a left femoral component. To this end, a distal stem trial includes an elongated stem having a terminal end and a connection end. The terminal end includes a deformation formed therewith. The connection end includes an attachment device including a threaded member and a resiliently mounted orientation member.

A principal advantage of this embodiment is the reduction of inventory and ease of broaching and trialing during surgery. Instead of using a left and right broach and stem trial, the surgeon has the ability to use the proximal broach which is part of the instrument set, and mechanically assemble the broach with the correct size distal stem trial for use in either a right or a left orientation.

BRIEF DESCRIPTION OF THE DRAWING FIGURES

FIG. 1 is a side view illustrating an embodiment of a stem trial.

FIG. 2 is another side view illustrating an embodiment of the stem trial.

FIG. 3 is a partial cross-sectional view of the stem trial taken along line 3—3 of FIG. 2.

FIG. 10 is a side view illustrating an embodiment of a broach disengaged from the stem trial.

FIG. 11 is another side view illustrating an embodiment of the broach.

FIG. 12 is an end view of the broach taken along line 12—12 of FIG. 11.

FIG. 13 is a side view illustrating an embodiment of the broach engaged with the stem trial.

DETAILED DESCRIPTION

Figure 4:
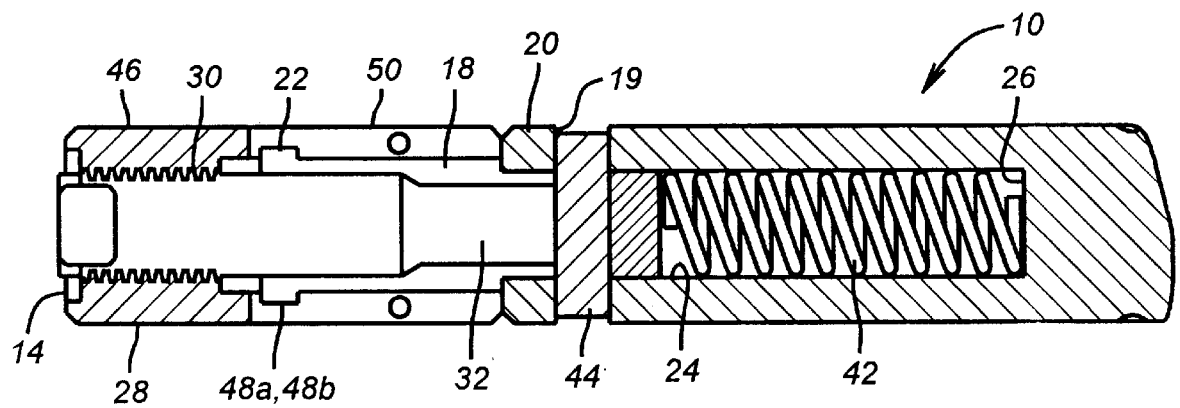
FIG. 4 is an enlarged partial cross-sectional view illustrating an embodiment of "the trial stem of FIG. 1 with the addition of an attachment device attached to the connection end" in lieu thereof.

A distal stem trial, FIGS. 1 and 2, includes an elongated stem 10 having a terminal end 12 and a connection end 14. Terminal end 12 includes a deformation having a planar chamfer surface 16 to permit first end 12 to avoid interfering with the anterior wall of the intramedullary canal during trialing. Connection end 14 of stem 10 includes an extension 18 having an annular flange 20 at one end and an annular shoulder 22 at an opposite end. Extension 18, FIG. 3, also includes a blind bore 24 formed therein extending through extension 18 and partially into stem 10 for terminating at an endwall 26. An opening 19 is formed through stem 10 to receive a pin to be press fit therethrough, as discussed below.

Figure 5:
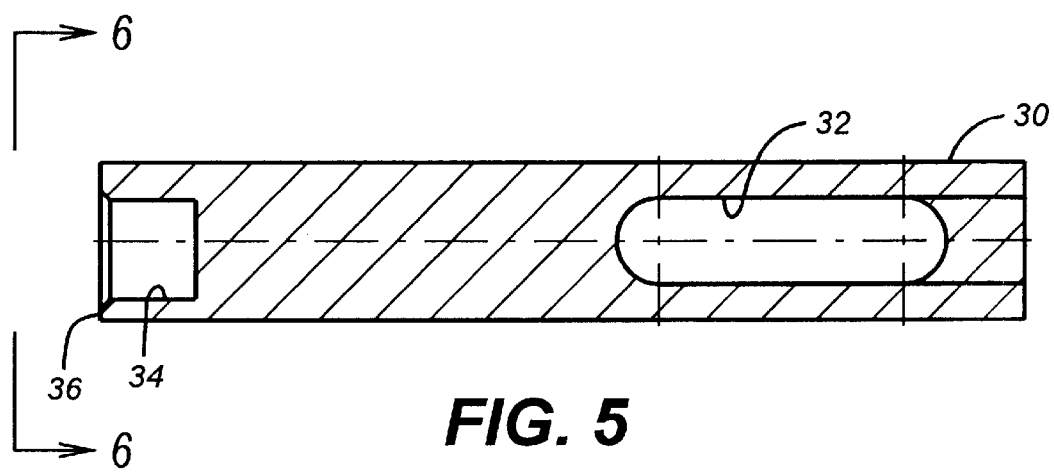
FIG. 5 is a cross-sectional side view illustrating an embodiment of an orientation member.
Figure 6:
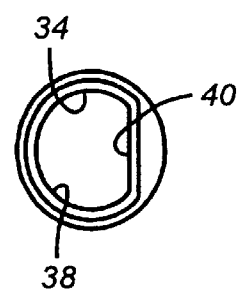
FIG. 6 is an end view of the orientation member taken along line 6—6 of FIG. 5.

Connection end 14, FIG. 4, includes an attachment device including a threaded member or collar 28 and a resiliently mounted orientation member 30. Orientation member 30, FIG. 5, is an elongated member having an elongated pin slot 32 extending transversely therethrough and an orientation bore 34 formed in one end 36 thereof. The orientation bore 34, FIG. 6, includes an annular sidewall 38 and a planar portion 40 formed therewith. Orientation member 30 is seated in blind bore 24, FIG. 3. A resilient member such as a compression spring 42, FIG. 4, is seated in blind bore 24 between orientation member 30 and endwall 26. A pin 44 extends in a press fit through stem 10, blind bore 24 and pin slot 32 to secure orientation member 30 in stem 10 and have limited resilient reciprocating movement in blind bore 24 due to the compression of spring 42 and the pin 44 extending through the elongated pin slot 32.

Figure 7:
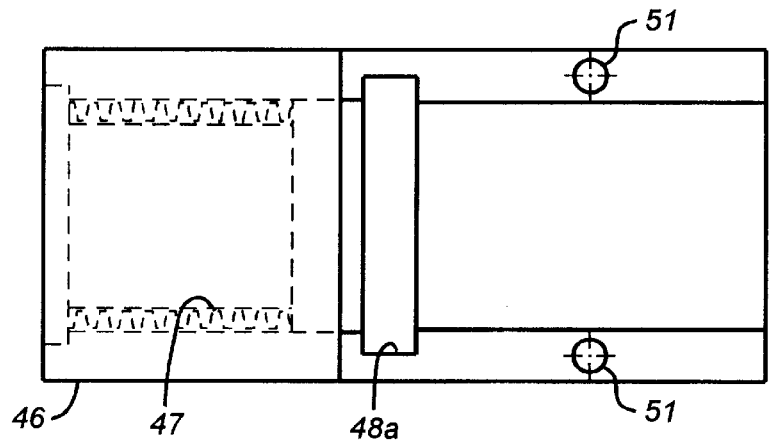
FIG. 7 is a side view illustrating an embodiment of a portion of a collar.
Figure 8:
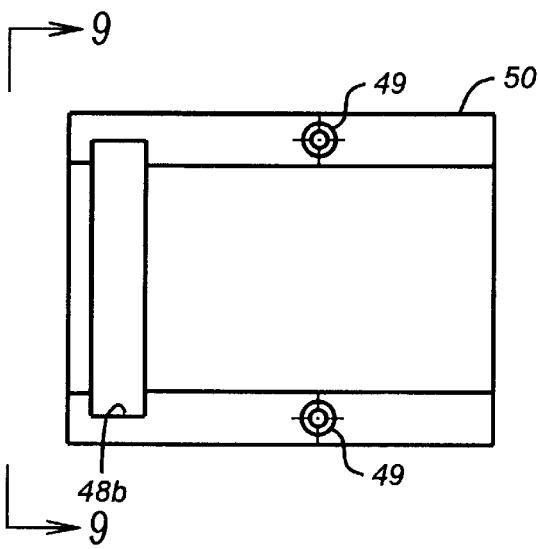
FIG. 8 is a side view illustrating an embodiment of another portion of the collar.
Figure 9:
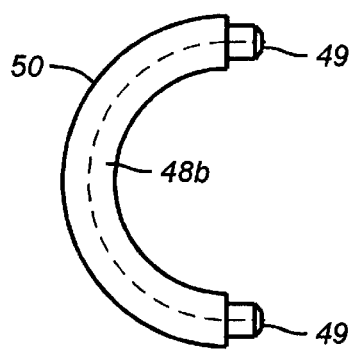
FIG. 9 is an end view of the collar taken along line 9—9 of FIG. 8.

Collar 28, FIG. 4, is rotatably mounted on flange 20, FIG. 3, of stem 10. This is accomplished by mounting a first portion 46, FIG. 7, of collar 28 on extension 18. First portion 46 includes a partial annular groove 48a, for receiving annular flange 20. First portion 46 also includes an internal threaded section 47. A second portion 50, FIG. 8, of collar 28 includes a complimentary partial annular groove 48b for cooperatively forming annular groove 48a, 48b, with partial groove 48a for receiving annular flange 20. A pair of locating pins 49, see also FIG. 9, in second portion 50 are seated in a pair of matched bores 51, FIG. 7, in first portion 46 to assure alignment of partial groove 48a and partial groove 48b. Second portion 50, FIG. 4, is welded to first portion 46 to form collar 28 into one piece secured for rotation on extension 18 due to the engagement of annular flange 20 within annular groove 48.

The connection end 14, FIG. 10, of stem 10 is provided for connection with a proximal broach trial 52 including an attachment device 54 at an end 56 thereof. Attachment device 54, see also FIG. 11, includes a threaded member 58 and an orientation member or tab 60 formed to extend from threaded member 58. Tab 60, FIG. 12, includes an annular outer sidewall 62 having a pair of substantially opposed planar portions 64a and 64b formed therewith. Planar portions 64a and 64b are angled toward each other to allow for a right and a left anteversion angle α of about 10° when either portion 64a or 64b are engaged with planar portion 40 of orientation bore 34, FIG. 6.

In operation, instead of using a left and a right broach with a stem trial, the surgeon has the ability to use the proximal broach trial 52 and mechanically assemble the broach 52, FIG. 13, with the distal stem trial 10 in either a left or right orientation. Broach 52 is attached to stem 10 by means of engaging planar portion 64a, FIGS. 6 and 12, of tab 60 with planar portion 40 of orientation bore 34 for one of a right or left orientation, or by engaging planar portion 64b of tab 60 with planar portion 40 of orientation bore 34 for the other of a right or left orientation. More specifically, broach 52 and stem 10 are attached by inserting tab 60 into bore 34 so that planar portion 40 engages, for example, planar portion 64a for a desired orientation. Collar 28 is then rotated to engage threaded section 47, FIG. 7, with threaded member 58, FIG. 11. For removal, collar 28 is rotated to detach threaded section 47 and threaded member 58, and tab 60 is removed from bore 34. Broach 52 and stem 10 are re-attached in another orientation by re-inserting tab 60 into bore 34 so that planar portion engages, for example, planar portion 64b. Collar 28 is then rotated as before to engage threaded section 47 with threaded member 58.

As a result, one embodiment provides a distal stem trial comprising an elongated stem having a terminal end and a connection end. The terminal end includes a deformation formed therewith. The connection end includes an attachment device including a threaded member and a resiliently mounted orientation member.

Another embodiment provides a universal distal stem trial comprising an elongated stem having a terminal end and a connection end. The terminal end includes a deformation useable with a left femur and a right femur. The connection end includes an attachment device for connection with a broach in a first orientation and a second orientation. The attachment device includes a rotatable threaded member and an orientation member resiliently mounted for reciprocating movement.

Another embodiment provides a combination stem trial and broach wherein the broach includes a first attachment device at one end thereof, having a first threaded member and a first orientation member. The elongated stem trial includes a second attachment device at a first end thereof for engagement with the first attachment device. The second attachment device includes a second threaded member for connection with the first threaded member and a second orientation member for connection with the first orientation member.

A further embodiment provides a method of attaching a stem trial to a broach including providing a first attachment device at one end of a broach including a first threaded member and a first orientation member. A second attachment device is provided at a first end of an elongated stem trial including a second threaded member and a second orientation member. The broach is attached to the elongated stem in a first orientation by engaging the first and second orientation members in a first orientation, and by securing the first and second orientation members with the first and second threaded members.

As it can be seen, the principal advantages of these embodiments are the reduction of inventory and ease of broaching and trialing during surgery. Instead of using a left and right broach and stem trial, the surgeon has the ability to use the proximal broach which is part of the instrument set, and mechanically assemble the broach with the correct size distal stem trial for use in either a right or a left orientation. The broach is attached to the distal stem trial by means of an orientation feature which aligns the distal stem trial for either a left or right component. Once the orientation is established, the surgeon can manually thread the stem and broach together to secure the stem to the broach so that the distal stem trial and broach do not separate during broaching or trialing. Actually, a quick connection device as described herein may be used for many interconnections between first and second members where one of the members can be mounted in either a first or a second orientation, or multiple orientations relative to the other member.

Although illustrative embodiments have been shown and described, a wide range of modification change and substitution is contemplated in the foregoing disclosure and in some instances, some features of the embodiments may be employed without a corresponding use of other features.

Accordingly, it is appropriate that the appended claims be construed broadly and in a manner consistent with the scope of the embodiments disclosed herein.

What is claimed is:

1. A distal stem trial, comprising:

an elongated stem body extending from a terminal end to a connection end and having a bore extending from the connection end into the body;

a spring located inside the bore;

an elongated orientation member having a first end positioned inside the bore and biased against the spring and a second end having a bore; and a collar rotatably mounted on the connection end of the stem body.

2. The distal stem trial of claim 1 in which the orientation member includes a slot adapted to receive a pin.

3. The distal stem trial of claim 2 in which the slot has an elongated configuration and extends completely through the orientation member.

4. The distal stem trial of claim 1 in which the bore at the first end of the orientation member has a non-circular configuration.

5. The distal stem trial of claim 4 in which the bore has a cross section that is partially circular with a planar side.

6. The distal stem trial of claim 1 in which the orientation member is adapted to move in a longitudinal direction in the bore of the stem body.

7. The distal stem trial of claim 6 in which the spring abuts against one end of the orientation member and biases it toward the connection end.

8. The distal stem trial of claim 6 in which the orientation member includes an elongated slot with a length, and the orientation member is adapted to move in the bore a distance equal to the length of the slot.

9. The distal stem trial of claim 8 in which the stem trial further includes a pin that extends through the stem body and into the slot of the orientation member.

10. The distal stem trial of claim 1 in which the connection end of the stem body includes an annular shoulder at one end.

11. The distal stem trial of claim 1 in which the second end of the orientation member extends outwardly from the connection end of the stem body.

12. The distal stem trial of claim 1 in which the collar comprises two parts, a first part extends around the connection end of the stem body, and a second part extends around the orientation member.

13. The distal stem trial of claim 12 in which the first and second parts abut against each other.

14. The distal stem trial of claim 12 in which the second end of the orientation member extends outwardly from an end of the second part of the collar.

15. The distal stem trial of claim 1 in which:

the stem body includes an opening adapted to receive a pin;

the orientation member includes an elongated slot that is aligned with the opening; and the stem trial further includes a pin positioned through the opening and into the slot.

16. A distal stem trial trial, comprising:

an elongate stem body extending from a terminal end to a connection end and having a bore extending from the connection end into the body;

a cylindrical orientation member located inside the bore and having a first end at the connection end, the first end having a shape adapted to engage a broach trial;

a means located in the bore for biasing the orientation member in an axial direction toward the connection end; and a collar rotatably mounted around the connection end of the stem body.

17. The stem trial of claim 16 in which the connection end of the stem body includes a flange, and the collar includes a groove adapted to rotatably engage the flange.

18. The stem trial of claim 16 in which:

the collar comprises a first and second part;

the first part has a cylindrical configuration and extends around the orientation member; and the second part has a cylindrical configuration with internal threads.

19. The stem trial of claim 18 in which the second part is adapted to threadably engage an end of the broach trial.

20. The stem trial of claim 16 in which:

the orientation member includes an slot;

the stem body includes an opening aligned with the slot;

the trial stem further comprises a pin that extends through the opening and into the slot.

21. The stem trial of claim 20 in which the pin is adapted to limit axial movement of the orientation member inside the bore of the stem body.

22. The stem trial of claim 16 in which the first end of the orientation member has an opening with a non-circular shape.

23. The stem trial of claim 22 in which the opening is adapted to engage an end of a broach trial.

* * * * *